United States Patent [19]

Layer

[11] Patent Number: 4,484,010

[45] Date of Patent: Nov. 20, 1984

[54] HYDROXYBENZYLCYCLOPENTADIENES AND DERIVATIVES THEREOF

[75] Inventor: Robert W. Layer, Cuyahoga Falls, Ohio

[73] Assignee: The B. F. Goodrich Company, Akron, Ohio

[21] Appl. No.: 456,921

[22] Filed: Jan. 10, 1983

[51] Int. Cl.$^3$ .............................................. C07C 39/17
[52] U.S. Cl. ..................................... 568/732; 568/731
[58] Field of Search ................................ 568/731, 732

[56] References Cited

U.S. PATENT DOCUMENTS

| | | | |
|---|---|---|---|
| 2,485,966 | 10/1949 | Good et al. | 568/731 |
| 2,852,568 | 9/1958 | Schmerling | 568/731 |
| 2,864,868 | 12/1958 | Bader | 568/731 |
| 3,118,953 | 1/1964 | Cutukovic | 568/731 |
| 3,379,775 | 4/1968 | Sheridan et al. | 568/731 |
| 3,683,033 | 8/1972 | Stockmann et al. | 568/731 |
| 3,689,573 | 9/1972 | Klein et al. | 568/731 |

FOREIGN PATENT DOCUMENTS

| | | | |
|---|---|---|---|
| 1092010 | 11/1960 | Fed. Rep. of Germany | 568/731 |
| 741446 | 12/1955 | United Kingdom | 568/731 |

*Primary Examiner*—Werren B. Lone
*Attorney, Agent, or Firm*—George A. Kap; Nestor W. Shust

[57] ABSTRACT

Hindered hydroxybenzylcyclopentadienes and derivatives thereof, useful as antioxidants, are prepared by reacting cyclopentadiene, an alkali metal, and a hindered p-methylphenol having a displaceable group attached to the methyl group in the presence of a non-protic solvent; or in one step, by reacting cyclopentadiene, hindered phenol that is devoid of a group in the para position, formaldehyde, an amine, water, and an alkali metal hydroxide in the presence of a phase transfer catalyst; or in one step, by reacting cyclopentadiene and a hindered substituted p-methyl-phenol containing a displaceable group, in the presence of a non-protic solvent, water, an alkali metal hydroxide and a phase transfer catalyst. These compounds readily dimerize whereas the bis compounds are prepared in presence of an excess amount of the substituted p-methylphenol.

17 Claims, No Drawings

HYDROXYBENZYLCYCLOPENTADIENES AND DERIVATIVES THEREOF

BACKGROUND OF THE INVENTION

Cyclopentadiene is present to the extent of about 15% in the naphtha cracker $C_5$ by-products stream from ethylene plants. One way to dispose of the $C_5$ by-products stream is to use it as a fuel stock, however, a better use is as a source of petrochemicals. The most sought-after component of the $C_5$ by-products stream is isoprene, which is also present at about 15% level. With the soaring price of natural rubber, pressure is mounting to expand synthetic polyisoprene production. For every pound of extract isoprene capacity that comes on stream, there will be a pound of cyclopentadiene. Thus, it stands to reason that with the sharp rise in the cost of crude oil, ethylene producers will have a strong incentive to find the most profitable uses for the by-products. In this context, cyclopentadiene is high on the list since its removal from the $C_5$ stream is easily accomplished at the first step of the $C_5$ purification process.

This invention pertains to reactions which involve cyclopentadiene in the formation of hydroxybenzylcyclopentadienes and derivatives thereof which are useful as antioxidants for stabilizing polymeric materials, and to processes for making such antioxidants.

The art of stabilizing polymeric materials is both complex and unpredictable. Ordinarily, the stabilizing agent is physically combined with the polymer thereby prolonging its useful life in the hostile degradative environment. In such cases, the stabilizing agent is generally free to slowly migrate within the composition and to the surface thereof. This presents a problem where the polymer is contacted by fluids which can extract the stabilizing agent. Furthermore, some stabilizing agents are very volatile and can change from a solid to a vapor at relatively low temperatures. Exposure of compositions containing such heat sensitive stabilizing agents will result in vaporization of the stabilizer and its eventual diffusion from the polymer. Whether the stabilizer is lost by fluid extraction or vaporization, or by any other means for that matter, the end result is that the polymer will become vulnerable to attack by degradative forces.

It is therefore desirable to have antioxidants which can be bound into the polymeric material to prevent its extraction, as by leaching, vaporization, or in any other similar fashion. The antioxidants herein have the capacity of being chemically bound into the polymeric material since they contain at least one double bond which can participate in an addition reaction with other polymeric materials during polymerization of the monomers or thereafter during curing when crosslinking would take place and finally during processing when a Diels-Alder reaction would bind the antioxidant to an unsaturated polymer such as cis-polybutadiene.

SUMMARY OF THE DISCLOSURE

Hindered hydroxybenzylcyclopentadienes and derivatives thereof, useful as antioxidants, are prepared by reacting cyclopentadiene or dicyclopentadiene, an alkali metal, and a hindered para methylphenol having attached to the methyl group a displaceable group selected from halogens, dialkylamino, hydroxy or alkoxy, acyloxy, and dithiocarbamyl and other displaceable groups. The antioxidants disclosed herein can also be prepared by reacting in one step cyclopentadiene, hindered phenol that is devoid of a group in the para position, formaldehyde, and an amine in presence of water and an alkali metal hydroxide; or else reacting in one step cyclopentadiene and hindered substituted p-methylphenol containing a displaceable group in the presence of a solvent, water and an alkali metal hydroxide. The monomeric antioxidants readily dimerize to form dimers whereas bis compounds are prepared in presence of an excess amount of the substituted p-methylphenol.

DETAILED DESCRIPTION OF THE INVENTION

The compounds disclosed herein can be easily made by reacting cyclopentadiene with a hindered p-methylphenol that contains a displaceable group, in presence of other materials such as an alkali metal or an alkali metal hydroxide catalyst. When using an alkali metal as the catalyst, the reaction must be conducted in absence of water. These compounds are effective antioxidants and can equal or exceed the commercial antioxidant BHT in antioxidant activity. BHT is 2,6-di-t-butyl-4-methylphenol. Furthermore, these compounds can be bound into polymers to improve effectiveness thereof as antioxidants due to the fact that they are relatively unextractable by conventional means.

The compounds referred to herein include the hindered hydroxybenzylcyclopentadienes or cyclopentadienyl phenols, defined by the following formula I:

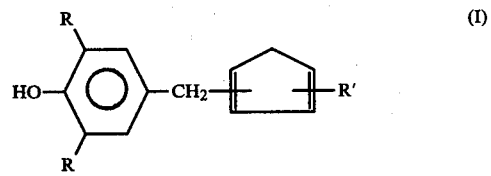

where the R groups are same or different and are selected from alkyl groups of 1 to 12 carbon atoms and substituted and unsubstituted alicyclic groups of 4 to 8 carbon atoms, preferably, alkyl groups of 1 to 6 carbon atoms, and more preferably, t-alkyl groups of 4 to 6 carbon atoms, especially t-butyl groups; and where there are up to five R' groups each individually selected from hydrogen and alkyl groups of 1 to 3 carbon atoms, preferably, there are up to three, and more preferably only one or no R' groups selected from alkyl groups of 1 to 3 carbon atoms, preferably methyl.

Preparation of the hydroxybenzylcyclopentadienes is carried out under anhydrous conditions. A mixture of cyclopentadiene, an alkali metal, and a hindered p-methylphenol with the methyl being substituted with a substituent which is a good leaving group, such as dimethylamino, in a non-protic solvent, is stirred for about 10 hours at about 60° C. The phenol reactant can be 2,6-di-t-butyl-4-dimethylaminomethylphenol, in which case, dimethylamine is liberated during the reaction. A sample is then analyzed to determine if all of the phenol has reacted. After workup, (3,5-di-t-butyl-4-hydroxybenzyl)cyclopentadiene is recovered by distillation having a boiling point of about 170° C. at 1.0 mm pressure in up to about 85% yield. To obtain a good yield of product, an excess of cyclopentadiene is used in the reaction. This, however, gives rise to a small amount of the following Diels-Alder condensation product (A):

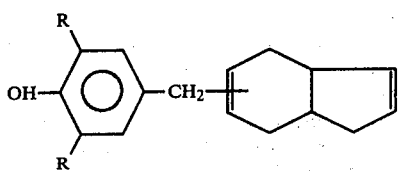

(A)

Compounds represented by formula (A), above, are the (3,5-dialkyl-4-hydroxylbenzyl)dicyclopentadienes, more generally, hindered (hydroxybenzyl) dicyclopentadienes.

The reaction described above can be carried out in the temperature range of 0° to 150° C., preferably 20° to 100° C., at atmospheric pressure. Higher reaction temperatures favor the formation of the unwanted by-products. Duration of the reaction can vary widely from less than one hour to couple of days, preferably 2 to 16 hours. Suitable non-protic solvents are benzene, toluene, xylene and tetrahydrofuran.

The same reaction occurs when 3,5-di-t-butyl-4-hydroxylbenzyl halide, dithiocarbamate or alkoxide is used in place of the p-dimethylaminomethylphenol reactant. Other substituents, which are good leaving groups, can also be used in this synthesis. Similarly, the same reaction occurs when methylcyclopentadiene is used in place of cyclopentadiene itself. Other substituted cyclopentadienes could also be used in this reaction.

The product of these reactions, the hindered hydroxybenzylcyclopentadiene (I), being a substituted cyclopentadiene, can be alkylated again. Thus, if an insufficient amount of cyclopentadiene is used, a relatively large amount of a bis(hindered hydroxybenzyl)cyclopentadiene is formed having the following structure II:

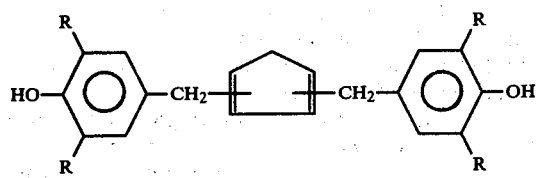

(II)

where the R groups are the same or different and are selected from alkyl groups of 1 to 12 carbon atoms and substituted and unsubstituted alicyclic groups of 4 to 8 carbon atoms, preferably, alkyl groups of 1 to 6 carbon atoms, and more preferably, t-alkyl groups of 4 to 6 atoms, especially t-butyl groups. When a very small amount of cyclopentadiene is used, or a very large excess of a hindered dialkylaminomethylphenol or its analog containing another displaceable group, the product is primarily bis(hindered hydroxybenzyl)cyclopentadiene of formula II and a very small amount of the trisubstituted compound and a significant amount of bis(hindered hydroxyphenyl)methane. It appears that two benzylic groups can be easily added to cyclopentadiene whereas addition of a third benzylic group is more difficult.

In a preferred case, the bis(hindered hydroxybenzyl)cyclopentadiene is obtained as the principal product when the (hindered hydroxybenzyl)cyclopentadiene (I), an alkali metal, and a hindered p-methylphenol containing a displaceable group, in a non-protic solvent, is stirred for 10 hours at 80° C. This reaction can be repeated using the bis(hindered hydroxybenzyl) cyclopentadiene (II) to give a tris(hindered hydroxybenzyl)-cyclopentadiene. Such repeated alkylation of the cyclopentadiene ring can result in a hexabenzylated product.

When a hindered hydroxybenzylcyclopentadiene is heated, dimer thereof is the primary product. This dimerization can take place at a temperature in a range of 0° to 200° C., preferably about 40° C., while duration of the reaction can vary in the range of 1 to 50 hours, preferably up to about two days, and more preferably about 24 hours. Furthermore, oscillographic scanning mass spectral analysis shows that some, less than 1 percent, of trimer and tetramer is also formed. The hindered hydroxybenzylcyclopentadiene is defined by the following general formula I and the dimer, trimer and tetramer thereof are defined by general formulas III, IV and V, below:

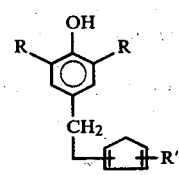

(I)

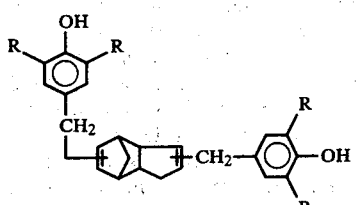

(III-dimer)

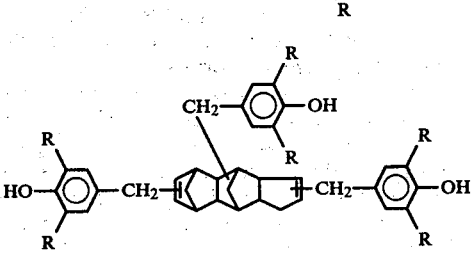

(IV-trimer)

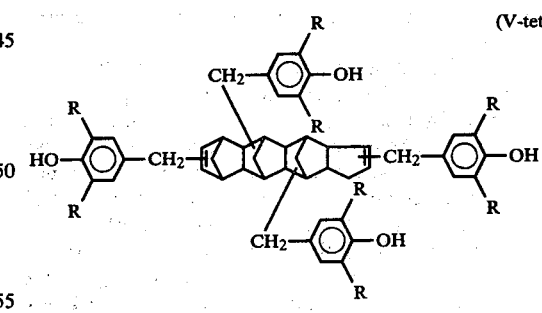

(V-tetramer)

The gas chromatographic analyses of the reaction mixtures are somewhat unusual. When the aminomethyl phenol is used as a reactant, the GC chart shows a distinct peak for the aminomethyl phenol followed by the cyclopentadienyl phenol, its dimer, etc. The unusual feature resides in the fact that the dimer slowly reverts to the cyclopentadienylphenol during its passage through the GC column. This manifests itself as a broad hump.

Another type of adduct can be obtained by reacting cyclopentadiene with a hindered hydroxybenzylcyclopentadiene or bis compounds thereof. This reaction also occurs when excess cyclopentadiene is used. This reaction can be carried out at 0° to 200° C. temperature in 1 to 50 hours, preferably at 80° C. for 24 hours, at atmospheric pressure. These reactions are depicted below:

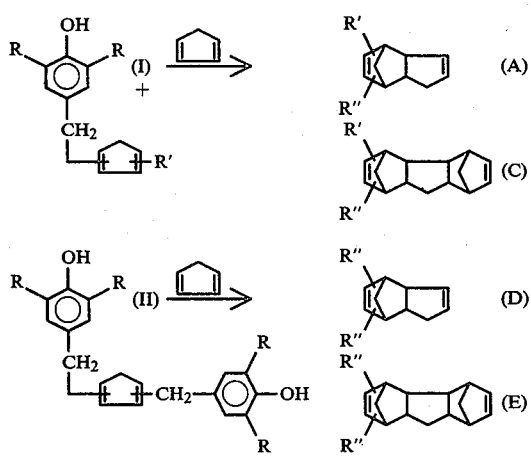

where R" is the group

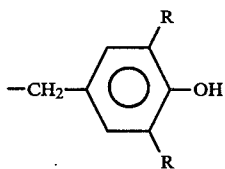

As already described, the reaction of an alkali metal, cyclopentadiene, and a hindered dialkylaminomethylphenol product forms hindered hydroxybenzylcyclopentadienes in good yields. This reaction can be improved in a number of practical respects. The main drawback of this reaction is the formation of water when the hindered dialkylaminomethylphenol is made, which must be removed in a separate step before the alkali metal can be added.

The problem with water can be avoided by using a phase transfer catalyst whereby a system can be used containing water, solvent and an alkali metal hydroxide instead of the alkali metal. In effect, product I, i.e., hindered hydroxybenzylcyclopentadiene, can be formed in one step from a hindered phenol. The phase transfer catalyzed reaction of a hindered dialkylaminomethylphenol with cyclopentadiene and an alkali metal can be carried out at a temperature of about 0° to 150° C., preferably 20° to 80° C., and for a duration of ½ to 4 days, preferably about 10 to 40 hours, while following the reaction with a gas chromatograph. Work up and distillation yields product I in about 40% yield.

Catalytic hydrogenation of the (cyclopentadienyl)phenols can give rise to molecules which are similar in activity to most commercial antioxidants. Hydrogenation is necessary to reduce the color of the (cyclopentadienyl)phenols which are somewhat yellow. The hydrogenated products are white. Secondly, dienes, especially conjugated dienes like cyclopentadiene, are easily oxidized. Consequently, the hydrogenated products, (cyclopentyl)phenols, would be expected to be better antioxidants than their unsaturated counterparts. Hydrogenation of products I and III proceeds rapidly at elevated temperature of about 50° to 200° C. but mass spectral analysis shows that some unsaturation remains. Hydrogenation of product I was carried out by dissolving it in a lower alkanol to retard dimerization thereof to product III. The saturated dimer, i.e., saturated product III, is the major product, whereas saturated product I is about one-third of the total product. It appears that the dimerization process occurs rapidly on warming and the use of a hydrogenation catalyst that is more active at lower temperatures should prevent or retard the dimerization. The pure reduced product I has a boiling point in the range of 131° to 160° C. at 0.7 mm pressure and the reduced product III, the reduced dimer, boils at 260° to 270° C. at 0.7 mm pressure.

It should be understood that cyclopentadiene slowly dimerizes to dicyclopentadiene at room temperature. Dicyclopentadiene is stable at room temperature. To obtain cyclopentadiene, the dicyclopentadiene is heated to about 160° C. and cyclopentadiene is removed. Dicyclopentadiene reacts at elevated temperature in the same manner as cyclopentadiene and can be used in its place yielding the corresponding compounds.

The following examples demonstrate the invention described herein in terms of preparation of certain of the novel compounds as well as their utility as antioxidants in synthetic elastomers. In the examples herein, a Hewlett-Packard Model 5710A gas chromatograph was used with 91.4×0.476 m, 10% UCW98 columns. The samples were temperature programmed at 16° C. per minute from 80° to 280° C.

EXAMPLE I

This example demonstrates preparation of a cyclopentadienylphenol, and specifically (3,5-di-t-butyl-4-hydroxybenzyl)cyclopentadiene, which is within the definition of formula I, above.

Sodium, in amount of 24 g (1.04 mol), was slowly added to a stirred solution of 158 g (0.6 m) of 2,6-di-t-butyl-4-dimethylaminomethylphenol and 132 g (2.0 m) of cyclopentadiene in 500 ml of tetrahydrofuran. The temperature was maintained at 30° C. by cooling during the addition of sodium, which took 1½ hours. The mixture was gradually heated to about 60° C. and it was held at this temperature overnight for about 16 hours. Dimethylamine was liberated during this time. Completion of the reaction was indicated by running a gas chromatograph analysis of a sample that showed that all of the aminomethyl phenol had reacted. The mixture was cooled to room temperature and treated with water and toluene. The upper toluene layer was separated, dried over sodium sulfate and rotovaped to remove the toluene and yield 238 g of black oil. Distillation of the black oil yielded 145 g (85%) of a yellow oil boiling in the temperature range of 165° to 233° C. at 1.5 to 1.9 mm pressure. Residue in an amount of 11 g remained. Gas chromatographic analysis of the distillate showed that it was relatively pure (3,5-di-t-butyl-4-hydroxybenzyl)cyclopentadiene and its dimer. It had the characteristic sharp peak for the monomer and the broad decomposition peak of the dimer in the gas chromatograph. Field desorption-mass spectral data showed that the product was a 1:2 mixture of the monomer to dimer, m/e 284 and m/e 568 respectively, with a small amount of disubstituted cyclopentadiene (II). The infrared spectrum had a hindered phenol OH band at 3650 cm-1.

EXAMPLE II

This example demonstrates the preparation of a substituted cyclopentadienyl phenol: methyl-(3,5-di-t-butyl-4-hydroxybenzyl)cyclopentadiene.

To a stirred mixture of 40 g (0.5 m) methylcyclopentadiene, 39.5 g (0.15 m) 2,6-di-t-butyl-4-dimethylaminophenol and 100 ml of tetrahydrofuran was slowly added 6.0 g (0.26 m) of sodium. The temperature was raised to 70° C. and the mixture allowed to react for 20 hours. A gas chromatograph showed that all of the 2,6-di-t-butyl-4-dimethylaminophenol had reacted. The mixture was diluted with water, extracted with toluene and rotovaped to remove the toluene and leave 38 g of crude product. A 90% yield, 31.5 g, of pure product methyl-(3,5-di-tert-butyl-4-hydroxybenzyl)cyclopentadiene was obtained by distillation, b.p. 155° to 160° C. at 1.5 mm as a viscous yellow oil. After standing at room temperature for 2 weeks, the material was analyzed by mass spectral analysis and by gas chromatography. Both showed that the product and its dimer were present. The mass spectrum showed a 3 to 1 ratio of the monomer to dimer, m/e 298 and m/e 596, respectively. The gas chromatograph showed a sharp peak for the monomer followed by the broad peak due to the slow decomposition of the dimer.

EXAMPLE III

This example demonstrates preparation of the cyclopentadienylphenol, (3,5-di-t-butyl-4-hydroxybenzyl)cyclopentadiene, by means of a phase transfer catalyzed reaction.

To a solution of 26.5 g (0.1 m) of (2,6-di-t-butyl-4-dimethylaminomethyl)phenol and 26.4 g (0.4 m) of cyclopentadiene in 200 ml of toluene containing 2 g of tri-caprylylmethylammonium chloride, a phase transfer catalyst, was slowly added a solution of 6 g (0.115 m) of sodium hydroxide in 50 ml of water at 20° C. After one hour, the mixture was heated to 60° C. and held at that temperature overnight for about 16 hours. Gas chromatographic analysis of a mixture sample showed that the aminomethyl phenol was no longer present, which indicated conclusion of the reaction. The reaction mixture was worked up in the usual way to yield 57.5 g of a dark oil which, upon distillation, gave 11.7 g (40% yield) of (3,5-di-t-butyl-4-hydroxybenzyl)cyclopentadiene boiling at 112° to 158° C. at 1.2 to 2.0 mm. A pot residue of 14.0 g remained.

EXAMPLE IV

This example demonstrates the preparation of bis-(3,5-di-t-butyl-4-hydroxybenzyl)cyclopentadiene.

To a stirred mixture of 24 g (0.09 mole) of freshly distilled (3,5-di-t-butyl-4-hydroxybenzyl)cyclopentadiene, 200 ml of tetrahydrofuran and 22 g (0.09 mole) of 2,6-di-t-butyl-4-dimethylaminophenol was added 4.0 g (0.2 mole) of sodium metal. The mixture was then heated at 65° C. for 24 hours, cooled, treated with water, extracted with toluene and the toluene rotovaped to leave 44 g of an oil. This was analyzed by mass spectral analysis and found to consist primarily of the desired bis-(3,5-di-t-butyl-4-hydroxybenzyl)cyclopentadiene, m/e 502, and some unreacted aminophenol. This crude product was hydrogenated, see example herein.

EXAMPLE V

This example demonstrates the condensation of (3,5-di-t-butyl-4-hydroxybenzyl)cyclopentadiene with cyclopentadiene.

To a stirred mixture of 19.5 g (0.3 mole) cyclopentadiene, 200 ml tetrahydrofuran, and 26.3 g (0.1 mole) of 2,6-di-t-butyl-4-dimethylaminophenol was slowly added 3 g (0.13 mole) of sodium metal. After the addition was complete, the mixture was heated at 65° C. for 24 hours. The mixture then was treated with water, extracted with toluene, the toluene rotovaped to leave 33 g of crude product. Field desorption mass spectral analysis showed that the desired adduct, (3,5-di-t-butyl-hydroxybenzyl)dicyclopentadiene, m/e 350, represented about 40% of the product, a small amount of compound I, m/e 284, was also present and the remainder was the dimer of I, i.e., III, m/e 568.

EXAMPLE VI

This example demonstrates hydrogenation of (3,5-di-t-butyl-4-hydroxybenzyl)cyclopentadiene, i.e., cyclopentadienylphenol.

A sample of 15 g of the cyclopentadienylphenol was dissolved in 150 ml of ethanol and hydrogenated at 100° C. using 3 g of Raney nickel as the catalyst. The reduction was very rapid and occurred during the warm-up period of ¼ hour. FD-MS analysis showed that about equal amounts of the completely hydrogenated products of I and III, m/e 288 and m/e 572, respectively, were formed as the major products. Minor amounts of partially reduced compounds were also present. The crude product was distilled to yield 5.0 g of the pure monomer product boiling at 131° to 160° C. at 0.7 mm and 3.27 g of the dimer product boiling at 260° to 271° C. at 0.7 mm. The NMR spectra were consistent with the monomer and dimer structures, and FD/EI/AC MS agreed to within 1 ppm of the calculated value. Calculated for the monomer ($C_{20}H_{32}O$) was 288.2453 and measured was 288.2453. Calculated for the dimer ($C_{40}H_{60}O_2$) was 572.4593, found to be 572.4598. Similar results were obtained when ruthenium on charcoal was used as the catalyst at 100° C.

EXAMPLE VII

This experiment demonstrates hydrogenation of the dimer of (3,5-di-t-butyl-4-hydroxybenzyl)cyclopentadiene.

The dimer was formed by heating 35 g of the monomer at 180° C. in a rocking bomb for 10 hours. The resulting dimer was then cooled to 30° C. temperature, and 100 ml of ethanol and 3 g of Raney nickel catalyst were added, and the dimer was hydrogenated in the usual way at 100° C. After removing the catalyst, 35 g of a solid product was obtained after treatment with water. FD-MS analysis showed that only the reduced dimer was present. The solid melted at 70° to 115° C., since it is a mixture of isomers of the reduced dimer.

EXAMPLE VIII

This example demonstrates the hydrogenation of bis-(3,5-di-t-butyl-4-hydroxybenzyl)cyclopentadiene.

The crude product of Example IV (44 g) was dissolved in 300 ml of ethanol and hydrogenated at 110° C. using 10 g of Raney nickel as the catalyst. The reduction occurred during the first hour of heating. The catalyst was removed by filtration, the ethanol removed by distillation to leave 38 g of crude product. Vacuum distillation gave 21 g (41% yield) of bis-(3,5-di-t-butyl-4-hydroxybenzyl)cyclopentane, b.p. 230° C. at 0.15 mm which was proven by mass spectral analysis to be the hydrogenated product, m/e 506.

EXAMPLE IX

This example demonstrates evaluation of certain of the compounds disclosed herein as antioxidants in re-precipitated natural rubber, i.e., polyisoprene or SN rubber.

In each instance, 0.68 g of a given antioxidant compound was mixed with 68 g of polyisoprene rubber in a Brabender Plasticorder for 2 minutes at 80° C. No antioxidant was added to the control sample. Each sample was prepared and tested for Mooney viscosity before and after aging pursuant to ASTM D-1646-72 test using a large rotor and 1-minute warm-up time. Mooney buttons were aged at 70° C. for 10 days in an oven, as prescribed by ASTMD-573-67 test. Table 1, below, summarizes results of these tests in terms of viscosity retention:

TABLE 1

| Additive | % Viscosity Retention |
| --- | --- |
| None | 20 |
| BHT | 66 |
| Reduced Compd. I | 81 |
| Dimer Compd. III | 56 |
| Reduced Dimer-Compd. III | 71 |
| Methyl Compound | 88 |

In the above table, BHT is a commercial antioxidant (4-methyl-2,6-di-t-butyl)phenol; Reduced Compd. I is (3,5-di-t-butyl-4-hydroxybenzyl)cyclopentane; Dimer Compd. III is the dimer of Compound I; Reduced Dimer Compd. III is saturated Dimer Compd. III, and Methyl Compd. is compound I with a methyl group on the cyclopentadiene ring. To facilitate understanding of the above results, some of the tested compounds are illustrated below by structural formulas where t-C4 represents a tertiary butyl group.

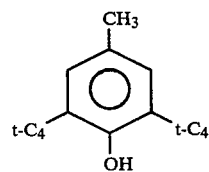

BHT

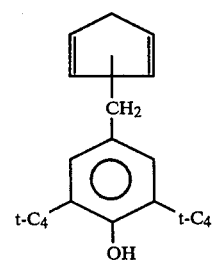

(I)

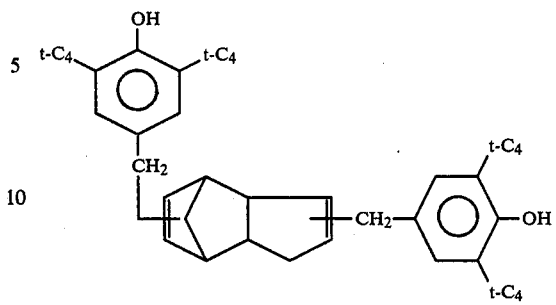

(III)

I claim:

1. Compounds defined by the following formula I, derivatives thereof, and mixtures of compounds of formula I and its derivatives

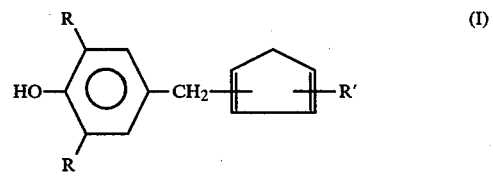

where the R groups are individually selected from alkyl groups of 1 to 12 carbon atoms and substituted and unsubstituted alicyclic groups of 4 to 8 carbon atoms, and there are up to 5 R' groups per each 5-membered ring, each individually selected from hydrogen and alkyl groups of 1 to 3 carbon atoms.

2. Compounds of claim 1 wherein in said compounds of formula I, said R groups are individually selected from alkyl groups of 1 to 6 carbon atoms; said derivatives are selected from bis compounds, dimers, trimers and tetramers defined by the respective formulas II, III, IV and V, below:

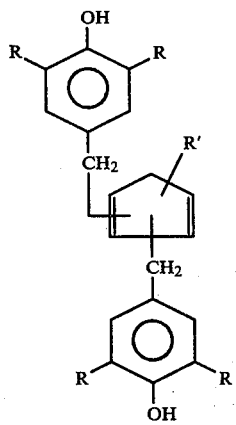

-continued

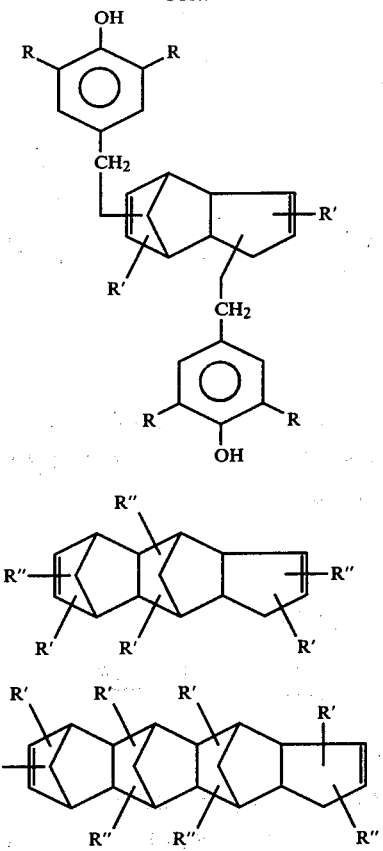

(III)

(IV)

(V)

where the R" group represents

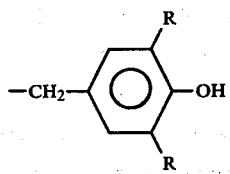

3. Compounds of claim 2 wherein each R group is individually selected from tertiary alkyl groups containing 4 to 6 carbon atoms, and wherein there are up to two of R' groups per each 5-membered ring each individually selected from alkyl groups of 1 to 3 carbon atoms.

4. Compounds of claim 2 selected from compounds defined by formulas I and II wherein each R group is individually selected from tertiary alkyl groups of 4 to 6 carbon atoms, and wherein there are up to two R' groups per each 5-membered ring each being individually selected from alkyl groups of 1 to 3 carbon atoms.

5. Compounds of claim 4 wherein all R groups are tertiary butyl and all R' groups are hydrogens.

6. Compounds of claim 4 in a hydrogenated state.

7. Compounds of claim 1 wherein in said compounds of formula I, said R groups are individually selected from tertiary alkyl groups of 4 to 6 carbon atoms, and wherein there are up to two R' groups per each 5-membered ring each being individually selected from alkyl groups of 1 to 3 carbon atoms; and said derivatives are selected from hydroxybenzyldicyclopentadienes of formula (A), and oligomers defined by formulas (C), (D) and (E), below:

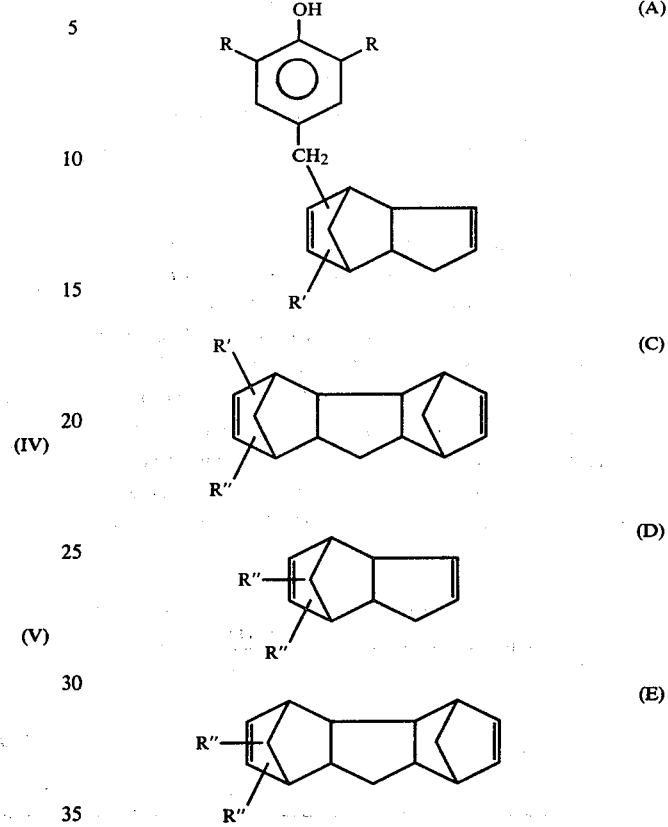

where R and R' groups are as defined herein and R" group represents

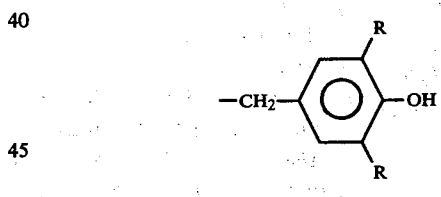

8. Compounds of claim 7 wherein all R groups are tertiary butyl and all R' groups are hydrogens.

9. Compounds of claim 7 in a hydrogenated state.

10. Composition comprising a polymeric material containing a sufficient amount for antioxidant activity of a compound defined by the following formula I and its derivatives

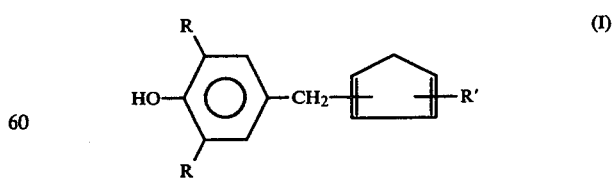

where the R groups are individually selected from the alkyl groups of 1 to 12 carbon atoms and substituted and unsubstituted alicyclic groups of 4 to 8 carbon atoms, and there are up to 5 R' groups per each 5-membered ring, each individually selected from hydrogen and alkyl groups of 1 to 3 carbon atoms.

11. Composition of claim 10 wherein in said compounds of formula I, said R groups are individually selected from alkyl groups of 1 to 6 carbon atoms; said derivatives are selected from bis compounds, dimers, trimers and tetramers defined by the respective formulas II, III, IV, and V, below:

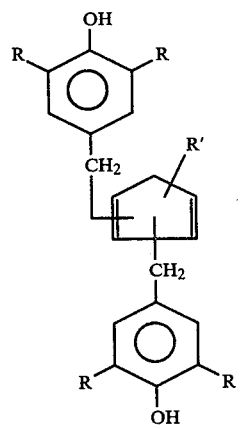 (II)

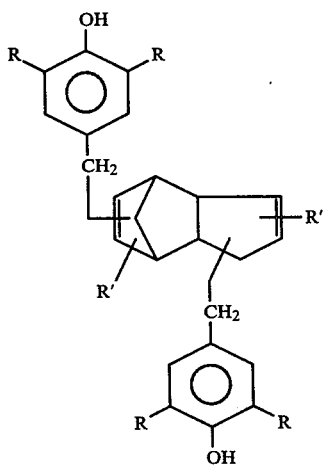 (III)

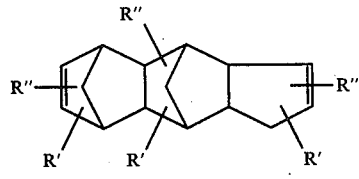 (IV)

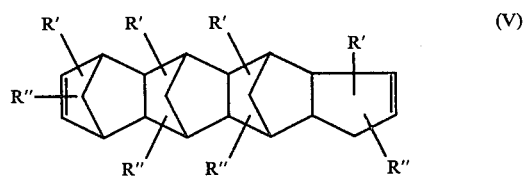 (V)

where the R″ group represents

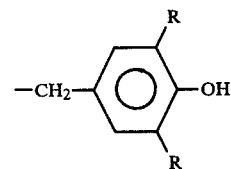

12. Composition of claim 11 wherein each R group is individually selected from tertiary alkyl groups containing 4 to 6 carbon atoms, and wherein there are up to two of R′ groups per each 5-membered rings each individually selected from alkyl groups of 1 to 3 carbon atoms.

13. Composition of claim 12 wherein the compounds are selected from compounds defined by formulas I and II wherein each R group is individually selected from tertiary alkyl groups of 4 to 6 carbon atoms, and wherein there are up to two R′ groups per each 5-membered ring each being individually selected from alkyl groups of 1 to 3 carbon atoms.

14. Composition of claim 11 wherein the compounds are selected from compounds defined by formulas I and II wherein each R group is individually selected from tertiary alkyl groups of 4 to 6 carbon atoms, and wherein there are up to two R′ groups per each 5-membered ring each being individually selected from alkyl groups of 1 to 3 carbon atoms.

15. Composition of claim 14 wherein said compound is in a hydrogenated state.

16. Composition of claim 11 wherein said polymeric material is selected from unsaturated polymeric materials.

17. Composition of claim 11 wherein said polymeric material is selected from polyisoprene.

* * * * *